(12) United States Patent
Gerhardt

(10) Patent No.: US 8,943,887 B2
(45) Date of Patent: Feb. 3, 2015

(54) THERMAL-BASED FLOW SENSING APPARATUSES AND METHODS FOR HIGH-PERFORMANCE LIQUID CHROMATOGRAPHY

(75) Inventor: Geoff C. Gerhardt, Milbury, MA (US)

(73) Assignee: Waters Technologies Corporation, Milford, MA (US)

( * ) Notice: Subject to any disclaimer, the term of this patent is extended or adjusted under 35 U.S.C. 154(b) by 292 days.

(21) Appl. No.: 13/512,762

(22) PCT Filed: Dec. 16, 2010

(86) PCT No.: PCT/US2010/060734
§ 371 (c)(1),
(2), (4) Date: Aug. 17, 2012

(87) PCT Pub. No.: WO2011/075570
PCT Pub. Date: Jun. 23, 2011

(65) Prior Publication Data
US 2012/0304746 A1    Dec. 6, 2012

Related U.S. Application Data

(60) Provisional application No. 61/287,949, filed on Dec. 18, 2009, provisional application No. 61/288,044, filed on Dec. 18, 2009, provisional application No. 61/288,024, filed on Dec. 18, 2009.

(51) Int. Cl.
*G01F 1/68* (2006.01)
*G01N 30/32* (2006.01)
*G01F 1/684* (2006.01)

(52) U.S. Cl.
CPC .............. *G01N 30/32* (2013.01); *G01F 1/6845* (2013.01); *G01N 2030/324* (2013.01)
USPC ...................................... 73/204.11

(58) Field of Classification Search
USPC .............. 73/204.24, 204.23, 204.36, 204.27, 73/204.15, 204.11
See application file for complete search history.

(56) References Cited

U.S. PATENT DOCUMENTS

2002/0121137 A1* 9/2002 Fujiwara et al. ........... 73/204.26
2004/0145049 A1* 7/2004 McKinnell et al. ........... 257/719
(Continued)

FOREIGN PATENT DOCUMENTS

| WO | WO-2008080106 A1 | 7/2008 |
| WO | PCT/ISA/210 | 2/2011 |
| WO | PCT/ISA/237 | 2/2011 |
| WO | WO-2011075568 | 6/2011 |
| WO | WO-2011075571 | 6/2011 |

OTHER PUBLICATIONS

International Preliminary Report on Patentability for PCT/US2010/060729 (WO 2011/075568), issued on Jun. 19, 2012 (7 pages).
(Continued)

*Primary Examiner* — Jewel V Thompson
(74) *Attorney, Agent, or Firm* — Edwards Wildman Palmer LLP; Nicholas DiCeglie; George N. Chaclas

(57) ABSTRACT

One aspect of the invention provides a flow sensing apparatus including: a fluid channel that allows a fluid to flow in a first direction; a first thermoelectric sensing element arranged at a first position along the fluid channel such that it senses a temperature of the fluid; a second thermoelectric sensing element arranged at a second position along the fluid channel and separated from the first sensing element by a predetermined distance along the fluid channel; and a heating element arranged between the first and second thermoelectric sensing elements, the heating element being equally spaced from the first and second thermoelectric sensing elements.

16 Claims, 4 Drawing Sheets

(56) References Cited

U.S. PATENT DOCUMENTS

| | | |
|---|---|---|
| 2004/0163957 A1 | 8/2004 | Neyer et al. |
| 2005/0109698 A1 | 5/2005 | Gerhardt et al. |
| 2005/0160833 A1 | 7/2005 | Gerhardt et al. |
| 2007/0034838 A1* | 2/2007 | Imaoka et al. ............... 252/500 |
| 2007/0265689 A1 | 11/2007 | Frey |
| 2008/0121576 A1 | 5/2008 | Gerhardt et al. |
| 2008/0145853 A1 | 6/2008 | Wu et al. |
| 2008/0245136 A1 | 10/2008 | Gerhardt et al. |
| 2009/0205409 A1 | 8/2009 | Ciavarini et al. |

OTHER PUBLICATIONS

International Preliminary Report on Patentability for PCT/US2010/060734 (WO 2011/075570), issued on Jun. 19, 2012 (7 pages).

International Preliminary Report on Patentability for PCT/US2010/060736 (WO 2011/075571), issued on Jun. 19, 2012 (7 pages).

* cited by examiner though the microfabricated type of flow sensor is sensitive and has a fast time response, it is costly to manufacture in small quantities due to the microfabrication process.

THERMAL-BASED FLOW SENSING APPARATUSES AND METHODS FOR HIGH-PERFORMANCE LIQUID CHROMATOGRAPHY

RELATED APPLICATIONS

This application is the U.S. national phase, pursuant to 35 U.S.C. §371, of PCT international application Ser. No. PCT/US2010/60734, filed Dec. 16, 2010, designating the United States and published in English on Jun. 23, 2011 as publication WO 2011/075570 A1, which claims priority to U.S. provisional patent application Ser. Nos. 61/287,949, filed Dec. 18, 2009; U.S. provisional application Ser. No. 61/288,044, filed Dec. 18, 2009; and U.S. provisional application Ser. No. 61/288,024, filed Dec. 18, 2009. The entire disclosures of all of the aforementioned patent applications are incorporated herein by this reference.

BACKGROUND OF THE INVENTION

In nano-scale liquid chromatography, it is generally desirable to achieve a low rate of elution of analytes. Although normal-scale High Performance Liquid Chromatography (HPLC) is performed with mobile phase flow rates of about 0.1 to 5.0 mL/min and micro-scale HPLC is performed with mobile phase flow rates of about 1 to 100 µL/min, nano-scale HPLC requires mobile phase flow rates approximately in the 50-1000 mL/min range. Generally, pumps used in nano-scale chromatography require sensitive and accurate flow rate information for control and monitoring purposes.

Fluid flow rates can be determined by measuring the thermal energy in the fluid. Many HPLCs employ thermal flow sensors to monitor flow rates.

The physical principle underlying some of these thermal sensors is the thermoelectric effect, and is also commonly known as the Seebeck effect. The Seebeck effect provides that a conductor subjected to a thermal gradient will develop a proportional electrical potential gradient. The magnitude of the electrical potential depends on a Seebeck coefficient of the conductor, which is an intrinsic property of the conductor. For example, if points A and B on a wire conductor are held at different temperatures $T_A$ and $T_B$, then an electrical potential E is created between points A and B and the magnitude of the electrical potential depends upon the Seebeck coefficient of the wire material.

A thermocouple is a conventional device for measuring thermoelectric effects, and FIG. 2A depicts a typical thermocouple configured to sense thermal energy. Materials A and B are subjected to a temperature gradient measured as two different temperatures $T_1$ and $T_2$. The resulting electrical potential V is the product of the differences between the Seebeck coefficients $S_A$ and $S_B$ and the differences between the temperatures $T_1$ and $T_2$, as illustrated by the equation below:

$$V=(S_B-S_A)(T_2-T_1)$$

If the Seebeck coefficients of materials A and B are known, and $T_1$ is held at a known temperature, the temperature $T_2$ can be determined by solving the above equation for $T_2$, or:

$$T_2=T_1+V/(S_B-S_A)$$

Therefore, the temperature $T_2$ can be calculated by measuring the voltage V and holding $T_1$ at some known temperature. Furthermore, commonly used thermocouple materials have stable, linear, and well-understood thermoelectric properties for a defined temperature range. Accurate temperature measurements can be made using conventional thermocouple materials. For Example, type-K thermocouples constructed with Chromel and Alumel are the most commonly used thermocouples. Type-N thermocouples constructed with Nicrosil and Nisil are commonly used for high-temperature application. Type-E thermocouples constructed with Chromel and Constantan are commonly used for cryogenic applications. These thermocouple materials are also relatively inert and can be used to make direct temperature measurements in a wide variety of environments.

However, existing thermal flow sensors capable of monitoring flows in approximately the nL/min ranges have various disadvantages. One class of thermal flow sensors tightly wrap a fine coil of resistance wire around the tube to measure temperature. This design can be difficult to manufacture because the fine coil must be precisely placed along the tube and consistently make contact with the tube. In addition, due to its large thermal mass, a lengthy coil and therefore a bulky coil is required to overcome its slow response to flow rate changes.

Another class of thermal sensors bonds an extremely small micro-fabricated device that contains two temperature sensors and heating element on one chip to a tube. Although the microfabricated type of flow sensor is sensitive and has a fast time response, it is costly to manufacture in small quantities due to the microfabrication process.

SUMMARY OF THE INVENTION

The subject invention provides thermal flow sensors that overcome the disadvantages associate with conventional thermal flow sensors.

Thus, in one aspect, the invention provides a flow sensing apparatus including: a fluid channel that allows a fluid to flow in a first direction; a first thermoelectric sensing element arranged at a first position along the fluid channel such that it senses a temperature of the fluid; a second thermoelectric sensing element arranged at a second position along the fluid channel and separated from the first sensing element by a predetermined distance along the fluid channel; and a heating element arranged between the first and second thermoelectric sensing elements, the heating element being equally spaced from the first and second thermoelectric sensing elements.

This aspect of the invention can have a variety of embodiments. The heating element can be supplied with a constant-power power supply. The flow sensing apparatus can include a controller that controls the power supplied to the heating element such that the temperature of the heating element is substantially constant. The first and second thermoelectric sensing elements can have substantially equal Seebeck coefficients. The first and second thermoelectric sensing elements can have equal Seebeck coefficients.

The first thermoelectric sensing element can have a Seebeck coefficient greater than a magnitude selected from the group consisting of about 200 µV/K, about 250 µV/K, about 300 µV/K, about 350 µV/K, about 400 µV/K, about 450 µV/K, about 500 µV/K, about 550 µV/K, about 600 µV/K, about 650 µV/K, about 700 µV/K, about 750 µV/K, about 800 µV/K, about 850 µV/K, about 900 µV/K, about 950 µV/K, about 1000 µV/K, about 1050 µV/K, about 1100 µV/K, about 1150 µV/K, about 1200 µV/K, about 1250 µV/K, about 1300 µV/K, about 1350 µV/K, about 1400 µV/K, about 1450 µV/K, about 1500 µV/K, about 1550 µV/K, about 1600 µV/K, about 1650 µV/K, about 1700 µV/K, about 1750 µV/K, about 1800 µV/K, about 1850 µV/K, about 1900 µV/K, about 1950 µV/K, and about 2000 µV/K.

The second thermoelectric sensing element can have a Seebeck coefficient greater than a magnitude selected from the group consisting of about 200 µV/K, about 250 µV/K, about 300 µV/K, about 350 µV/K, about 400 µV/K, about 450 µV/K, about 500 µV/K, about 550 µV/K, about 600 µV/K, about 650 µV/K, about 700 µV/K, about 750 µV/K, about 800 µV/K, about 850 µV/K, about 900 µV/K, about 950 µV/K, about 1000 µV/K, about 1050 µV/K, about 1100 µV/K, about 1150 µV/K, about 1200 µV/K, about 1250 µV/K, about 1300 µV/K, about 1350 µV/K, about 1400 µV/K, about 1450 µV/K, about 1500 µV/K, about 1550 µV/K, about 1600 µV/K, about 1650 µV/K, about 1700 µV/K, about 1750 µV/K, about 1800 µV/K, about 1850 µV/K, about 1900 µV/K, about 1950 µV/K, and about 2000 µV/K.

The first and second thermoelectric sensing elements can include one or more materials selected from the group consisting of: bismuth telluride, lead-germanium-selenium glasses, uranium oxides, thallium tin telluride, and thallium germanium telluride. The first thermoelectric sensing element can be doped with a N-type charge carrier and the second thermoelectric sensing element can be doped with a P-type charge carrier.

The first and second thermoelectric sensing elements can be discrete thermoelectric elements in an array of thermoelectric elements.

The flow sensing apparatus can include a controller that controls the power supplied to the heating element such that the heating element is maintained at a substantially constant temperature. The controller can be coupled to at least one of the first and the second thermoelectric sensing elements to sense the temperature of the heating element.

Another aspect of the invention provides a method of sensing a flow rate through a fluid channel having a first thermoelectric sensing element and a second thermoelectric sensing element equally spaced along the fluid channel from heating element. The method includes: actuating the heating element; flowing a sample through the fluid channel; receiving temperature information from the first thermoelectric sensing element and the second thermoelectric sensing element; and calculating a flow rate based on a difference in temperatures between the first thermoelectric sensing element and the second thermoelectric sensing element.

This aspect of the invention can have a variety of embodiments. The heating element can be supplied with a constant-power power supply. The method can include controlling the power supplied to the heating element such that the temperature of the heating element is substantially constant. The first and second thermoelectric sensing elements can have substantially equal Seebeck coefficients. The first and second thermoelectric sensing elements can have equal Seebeck coefficients.

The first thermoelectric sensing element can have a Seebeck coefficient greater than a magnitude selected from the group consisting of about 200 µV/K, about 250 µV/K, about 300 µV/K, about 350 µV/K, about 400 µV/K, about 450 µV/K, about 500 µV/K, about 550 µV/K, about 600 µV/K, about 650 µV/K, about 700 µV/K, about 750 µV/K, about 800 µV/K, about 850 µV/K, about 900 µV/K, about 950 µV/K, about 1000 µV/K, about 1050 µV/K, about 1100 µV/K, about 1150 µV/K, about 1200 µV/K, about 1250 µV/K, about 1300 µV/K, about 1350 µV/K, about 1400 µV/K, about 1450 µV/K, about 1500 µV/K, about 1550 µV/K, about 1600 µV/K, about 1650 µV/K, about 1700 µV/K, about 1750 µV/K, about 1800 µV/K, about 1850 µV/K, about 1900 µV/K, about 1950 µV/K, and about 2000 µV/K.

The second thermoelectric sensing element can have a Seebeck coefficient greater than a magnitude selected from the group consisting of about 200 µV/K, about 250 µV/K, about 300 µV/K, about 350 µV/K, about 400 µV/K, about 450 µV/K, about 500 µV/K, about 550 µV/K, about 600 µV/K, about 650 µV/K, about 700 µV/K, about 750 µV/K, about 800 µV/K, about 850 µV/K, about 900 µV/K, about 950 µV/K, about 1000 µV/K, about 1050 µV/K, about 1100 µV/K, about 1150 µV/K, about 1200 µV/K, about 1250 µV/K, about 1300 µV/K, about 1350 µV/K, about 1400 µV/K, about 1450 µV/K, about 1500 µV/K, about 1550 µV/K, about 1600 µV/K, about 1650 µV/K, about 1700 µV/K, about 1750 µV/K, about 1800 µV/K, about 1850 µV/K, about 1900 µV/K, about 1950 µV/K, and about 2000 µV/K.

In yet another aspect, the invention provides a kit comprising a flow sensing apparatus comprising: a fluid channel that allows a fluid to flow in a first direction; a first thermoelectric sensing element arranged at a first position along the fluid channel such that it senses a temperature of the fluid; a second thermoelectric sensing element arranged at a second position along the fluid channel and separated from the first sensing element by a predetermined distance along the fluid channel; and a heating element arranged between the first and second thermoelectric sensing elements, the heating element being equally spaced from the first and second thermoelectric sensing elements; and instructions for installation and/or use.

Still another aspect of the invention provides a High Performance Liquid Chromatography (HPLC) device comprising a flow sensing apparatus comprising: a fluid channel that allows a fluid to flow in a first direction; a first thermoelectric sensing element arranged at a first position along the fluid channel such that it senses a temperature of the fluid; a second thermoelectric sensing element arranged at a second position along the fluid channel and separated from the first sensing element by a predetermined distance along the fluid channel; and a heating element arranged between the first and second thermoelectric sensing elements, the heating element being equally spaced from the first and second thermoelectric sensing elements.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DETAILED DESCRIPTION OF THE INVENTION

A thermal flow sensor according to the subject invention utilizes the thermoelectric effect to convert thermal convection due to a flowing fluid into a voltage response that is proportional to the fluid flow rate.

Figure 2:
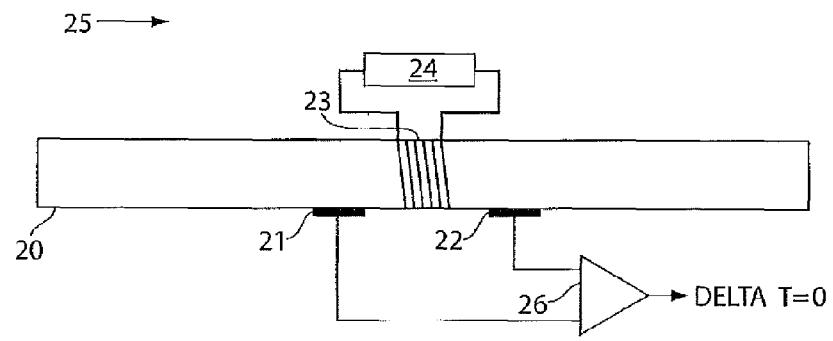
FIG. 2 is a schematic view of a thermal flow sensing apparatus.
Figure 2A:
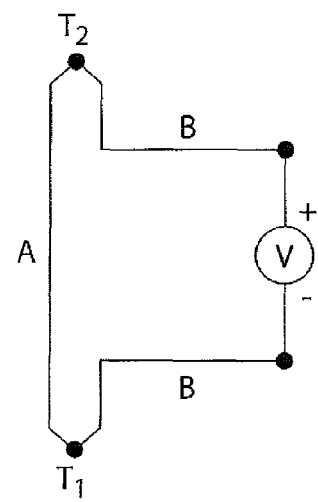
FIG. 2A is a schematic view of a thermocouple useful for measuring temperature.

FIG. 2 schematically depicts a thermal flow sensing apparatus. As shown in FIG. 2, a first temperature sensor 21 and a second temperature sensor 22 are disposed along a fluid channel 20, for example, a capillary tube or a micro-fluidic channel. The direction of fluid flow is denoted by an arrow 25, where the fluid generally flows from left to right in a downstream direction in FIG. 2. A heating element 23 powered by a heating power source 24 is disposed at a fixed location along the fluid channel and in between the first and second temperature sensors 21 and 22. As the heating element 23 introduces thermal energy into a fluid filled fluid channel 20, temperatures along the fluid channel 20 may be measured by positioning the first and second temperature sensors 21 and 22 along the fluid channel 20.

Figure 1:
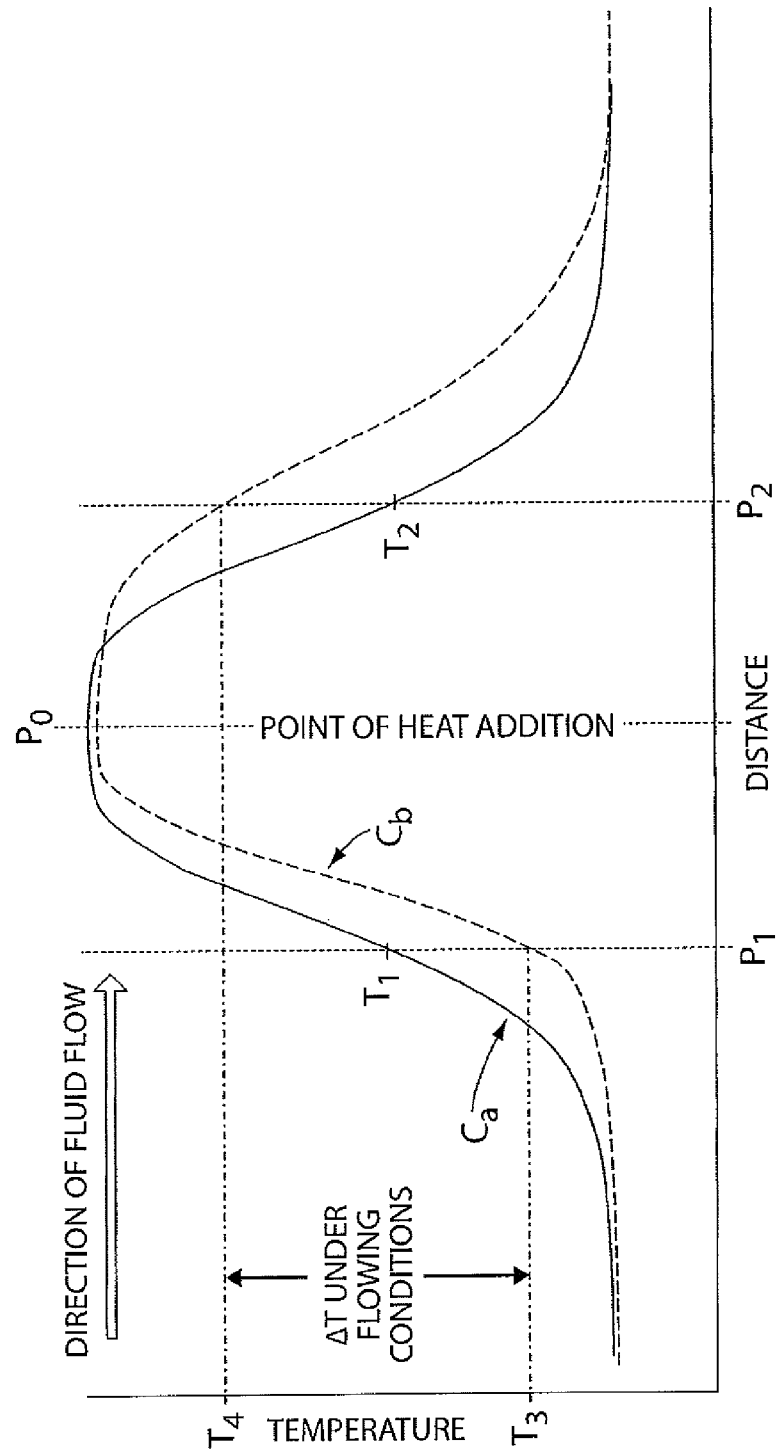
FIG. 1 is a conceptual view of thermal flow sensing measurements.

FIG. 1 depicts fluid temperature measurements along a fluid filled fluid channel 20 as thermal energy is introduced at a fixed location along the fluid channel 20. When thermal energy is introduced into a liquid filled fluid channel at location P0 along the channel 20, the thermal energy will disperse along the channel 20 in both the upstream and downstream directions due to thermal conduction and diffusion. In FIG. 1, the vertical axis denotes measured temperature and the horizontal axis denotes distance along the fluid channel 20. A temperature profile, curve $C_a$ will develop when a discrete section of the fluid in the fluid channel is continuously heated by the heating element 23 while the fluid is resting or under a so-called zero-flow condition. The shape of this temperature profile depends on the amount of heat added to the fluid and the upstream and downstream temperatures of the liquid. Assuming identical upstream and downstream fluid temperatures and a zero-flow condition, liquid temperatures T1 and T2 measured at the first and second sensors 21 and 22 that are placed at equal distances upstream and downstream from P0, denoted by P1 and P2, will be equal as thermal conduction and diffusion will be approximately equal.

If liquid in the fluid channel 20 is permitted to flow, the fluid temperatures at the first and second locations $P_1$ and $P_2$ will depend upon the flow rate of liquid and the resulting heat convection. Curve $C_b$ of FIG. 1 depicts a temperature profile as liquid begin to flow past $P_0$, or the heated zone. Note that while $C_a$ is substantially symmetrical about $P_0$, $C_b$ is not symmetrical about $P_0$. This is due to an asymmetric convection of the heated fluid that occurs in the direction of the fluid flow. Therefore, under flowing conditions, fluid temperatures $T_3$ and $T_4$ measured at $P_1$ and $P_2$, respectively, will be different from $T_1$ and $T_2$. A difference of $T_3$ and $T_4$, denoted by $\Delta T$, may be calculated and correlated to the actual flow rate of the fluid that flowed inside the fluid channel 20.

To perform the above-mentioned temperature measurements, a number of sensing methods and apparatuses may be used. Generally, two temperature sensors are disposed along a fluid channel at equal distances upstream and downstream from the heating element. For example, FIG. 2 depicts the first temperature sensor 21 and second temperature sensor 22 disposed along the fluid channel 20 such that the distance from the heating element 23 to the temperature sensor 21 in an upstream direction and the distance from the heating element 23 to the temperature sensor 22 in a downstream direction are approximately equal.

Temperature measurements made at the first and second sensors 21 and 22 can be sampled, subtracted and electronically amplified by using an amplifier element 26 to provide a signal with noise minimized by a high degree of common-mode noise rejection. This allows detection and discrimination of extremely small upstream and downstream temperature differences. Temperature measurement can be made at inflection points along the temperature profile by changing the placement of the first and second temperature sensors 21 and 22 and/or by changing the amount of thermal energy added to the liquid by the heating element 23. For example, as shown in FIG. 1, $P_1$ and $P_2$ were chosen to be the inflection points of the temperature profile $C_a$. Measurement at the inflection points can minimize the amount of time required to detect a difference between measured temperatures $T_1$ and $T_3$ or the difference between the temperatures $T_2$ and $T_4$ and thus maximize the upstream/downstream $\Delta T$ response of the amplifier element 26 to flow rate change.

Thermal flow sensing requires accurate measurement of relative temperature changes instead of absolute temperatures. Also, it may not be necessary for the temperature sensors to be in contact with the flowing fluid. Furthermore, the temperature difference in a flow sensor application will be relatively small (<10° C.) and the $\Delta T$ response to flow in a typical thermal flow sensor application has an inherently non-linear response. As a result, material that may have been rejected for a typical thermocouple application due to poor inertness or a narrow temperature range of linear response can be considered for a flow sensor application.

Peltier devices also rely on the thermoelectric effect to convert electrical energy to a thermal gradient. In order to create a large thermal gradient, Peltier devices typically use materials with very high Seebeck coefficients. Bismuth telluride is a common material used in Peltier devices and has a Seebeck coefficient of about $-287$ µV/C. This Seebeck coefficient is almost an order of magnitude above Seebeck coefficients for typical thermocouples, which are approximately 10-50 µV/C. Bismuth telluride cannot be used in a typical thermocouple application because it cannot be formed into a wire easily and does not have the required inertness. However, its high Seebeck coefficient may be ideal for flow sensing since its electrical potential response to the flow-induced thermal gradient is significantly higher than material used in typical thermocouples. Other suitable materials with high Seebeck coefficients include lead-germanium-selenium glasses, uranium oxides, thallium tin telluride ($Tl_2SnTe_5$) and thallium germanium telluride ($Tl_2GeTe_5$).

In order to increase the thermoelectric capacity of Peltier devices, it is common to electrically connect multiple bismuth telluride elements in series with their thermal gradients aligned. Also, bismuth telluride elements can be doped with charge carriers of opposite types to double the thermoelectric effect. For example, in FIG. 3, the Seebeck coefficients of the P-doped and N-doped materials 304 and 305 are identical but opposite in sign, so when electrically connected in series, the temperature gradient developed is doubled.

Therefore, the temperature-to-voltage response of a thermocouple configured to measure temperature can be enhanced by the use of multiple high Seebeck coefficient elements such as bismuth element. The enhanced temperature-to-voltage response can be further amplified by pairing oppositely-doped, high Seebeck coefficient elements in series. For example, pairing a N-doped bismuth telluride element with a P-doped bismuth telluride element in series doubles the temperature-to-voltage response and results in a highly sensitive temperature sensor.

Figure 3:
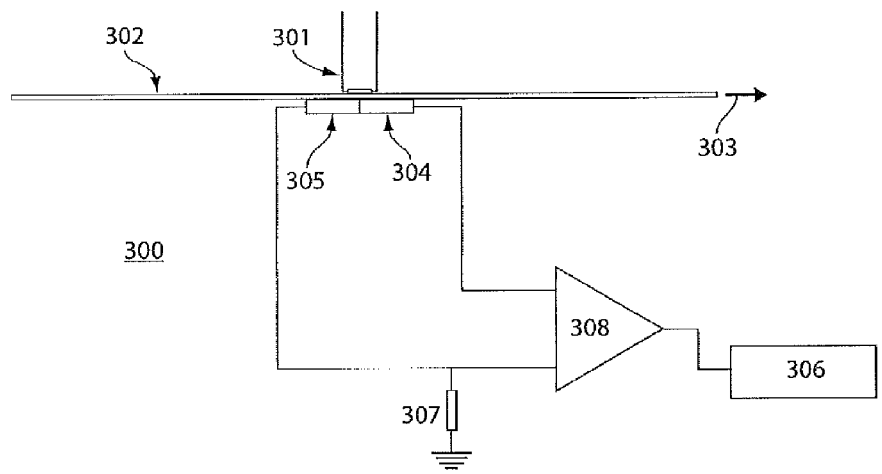
FIG. 3 is a schematic view of a thermal flow sensing apparatus including two thermoelectric sensors according to one embodiment of the invention.

FIG. 3 depicts one embodiment of a thermal flow sensing apparatus according to the invention in which doped thermoelectric elements are provided on a microfluidic chip 300. The microfluidic chip 300 includes first and second doped thermoelectric elements 304 and 305 arranged on a first side of the microfluidic chip end-to-end below a fluid channel 302 that allows fluid to flow in the direction indicated by an arrow 303. The first and second doped thermoelectric elements 304, 305 preferably are high Seebeck coefficient elements doped with opposite charge carriers. For example, the first doped thermoelectric element 304 may be a P-doped bismuth telluride pellet and the second doped thermoelectric element 305 may be a N-doped bismuth telluride pellet.

Next, a heating element 301 is bonded on a second side of the microfluidic chip above the fluidic channel and opposite the mating point of the first and second doped thermoelectric elements 304 and 305. Alternatively, the heating element may be bonded on the same side as the doped thermoelectric elements 304, 305, or at another location along the fluid channel 302.

The P-doped thermoelectric element 304 and the N-doped thermoelectric element 305 preferably are electrically coupled in series. Further, the paired thermoelectric elements 304 and 305 can be coupled to a biasing element 307 and a signal receiver/amplifier element 308 such that a voltage signal across the paired thermoelectric elements 304 and 305 are provided as input to the receiver/amplifier element 308. The output of the receiver/amplifier element 308 is coupled to a controller 306 for additional processing of the voltage signal. For example, if bismuth telluride pellets are used as the doped thermoelectric elements, fine wires soldered to the terminal end of the pellets may be used as a means to couple the thermoelectric elements.

Referring to FIGS. 1 and 2, the temperature profile along the fluid channel 20 extending away from the heating element 23 is substantially symmetrical under zero-flow conditions. In FIG. 3, as the heating element 301 provides thermal energy to the fluid channel 302 and the fluid inside the fluid channel 302, each of the P-doped and N-doped thermoelectric elements experiences a thermal gradient along its length, and each thermoelectric element produces an electric potential. The output of the amplifier will be zero because the Seebeck coefficients of the two thermoelectric elements 304 and 305 are equal but opposite in signs. When the fluid inside the fluid channel 302 is flowing, convection of the thermal energy due to fluid flow produces an asymmetric temperature profile along the two thermoelectric elements. The asymmetric temperature profile results in different thermal gradients in the thermoelectric elements and the output of the amplifier may be predicted using the following equation.

$$V = G \times (S_W(T_D - T_U) + S_P(T_H - T_D) + S_N(T_H - T_U))$$

In the equation above, G is the amplifier gain of the receiver/amplifier element 308, $S_W$ is the Seebeck coefficient of connecting wire that couples the pair of thermoelectric elements to the biasing element 307 and the receiver/amplifier element 308, $S_N$ is the Seebeck coefficient of N-doped thermoelectric element 305, $S_P$ is the Seebeck coefficient of P-doped thermoelectric element 304, $T_U$ is the upstream temperature experienced by N-doped thermoelectric element 305, $T_D$ is the downstream temperature experienced by the P-doped thermoelectric element 304, and $T_H$ is the temperature at heating element 301.

Since the Seebeck coefficients for the pair of thermoelectric elements 305 and 304 are opposite in signs, $S_P = -S_N$, we can reduce the equation above to the following equation.

$$V = G \times (S_W + S_N)(T_D - T_U)$$

In a thermal-base flow sensor, since fluid flow is proportional to the difference between the two temperatures $T_U$ and $T_D$ and the voltage is a product of known factors $G \times (S_W + S_N)$ and the difference between the two temperatures $(T_D - T_U)$, the voltage is also proportional to the fluid flow.

Figure 3A:
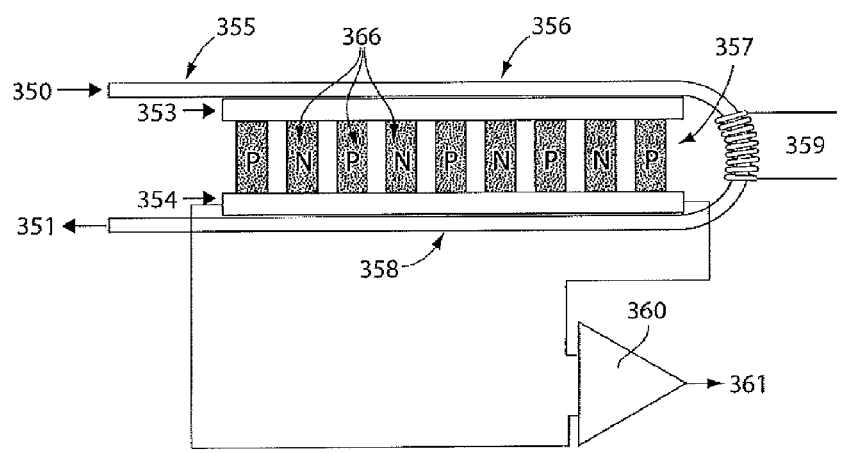
FIG. 3A is an schematic view of a thermal flow sensing apparatus according to another embodiment of the invention.

FIG. 3A depicts another embodiment of the subject invention. As shown in FIG. 3A, a standard "off-the-shelf" Peltier device 357 is used as a sensing element to sense a temperature of fluid flowing in a metal tubing 355. The fluid flows from an upstream direction 350 to a downstream direction 351. In this embodiment, the tubing 355 is bonded to a first side 356 and a second side 358 of the Peltier device. A resistance wire heater 359 is arranged on the tubing such that the resistance wire heater 359 heats a short section of tubing extending between the two sides 356 and 358. Typically, Peltier devices 357 may be constructed with metalized surfaces 353 and 354 so that metal tubing 355 may be soldered onto the surfaces 353 and 354 to improve a thermal contact between the metal tubing 355 and the Peltier device 357. In this configuration, multiple alternating P-doped and N-doped bismuth telluride elements 366 are arranged in series to form a Peltier stack to sense a temperature difference created between the two faces of the Peltier device 357. The temperature difference is created by the convection of the fluid flowing in the tube 357 as it passes through the heated section of the tube.

Figure 4:
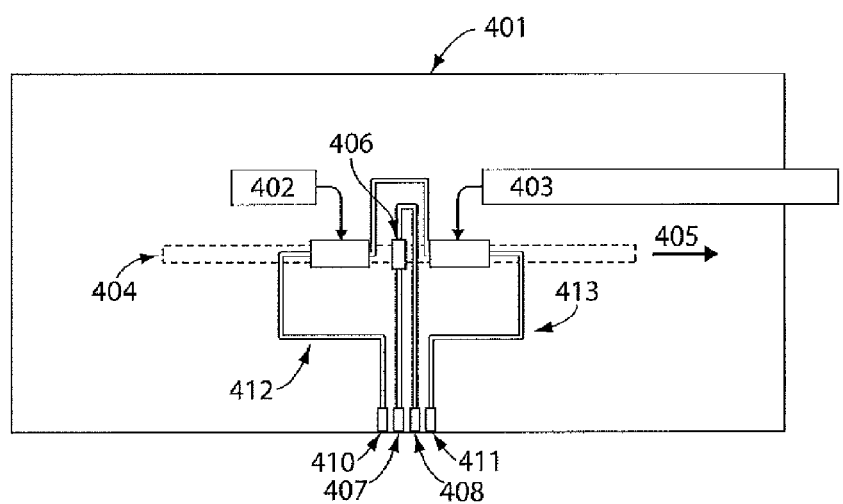
FIG. 4 is a plan view of a thermal flow sensing apparatus according to yet another embodiment of the invention.

According to a yet another embodiment of the subject invention, as shown in FIG. 4, a fluid channel may be formed on a microfluidic chip 401 constructed using low-temperature co-fired ceramics. A thick-film paste of N-doped and P-doped bismuth telluride may be used as thermoelectric sensing elements 402 and 403. A heating element 406 and the thermoelectric sensing elements 402 and 403 preferably are arranged on one surface of the microfluidic chip 401 such that the thermoelectric sensing element 402 senses a temperature along the fluid channel upstream from the heating element 406 and the thermoelectric sensing element 403 senses a temperature along the fluid channel downstream from the heating element 406. The heating element may be formed with a thick-film resistive heater, which has two terminals 407 and 408 arranged as contact terminals on the microfluidic chip. The thermoelectric sensing elements 402 and 403 are electrically connected in series by a surface connector 409 and each of the two thermoelectric sensing elements 402 and 403 are connected to contact terminals 410 and 411 by surface connectors 412 and 413. The surface terminal can be formed with conductor paste on a surface of the microfluidic chip.

INCORPORATION BY REFERENCE

The entire contents of all patents, published patent applications, and other references cited herein are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:
1. A flow sensing apparatus comprising:
a fluid channel that allows a fluid to flow in a first direction;
a first thermoelectric sensing element arranged at a first position along the fluid channel such that the first thermoelectric sensing element senses a temperature of the fluid, wherein the first thermoelectric sensing element is doped with a N-type charge carrier;
a second thermoelectric sensing element arranged at a second position along the fluid channel and separated from the first sensing element by a predetermined distance along the fluid channel, wherein the second thermoelectric sensing element is doped with a P-type charge carrier; and a heating element arranged between the first and second thermoelectric sensing elements, the heating element being equally spaced from the first and second thermoelectric sensing elements.

2. The flow sensing apparatus of claim 1, wherein the heating element is supplied with a constant-power power supply.

3. The flow sensing apparatus of claim 1, further comprising a controller that controls the power supplied to the heating element such that the temperature of the heating element is substantially constant.

4. The flow sensing apparatus of claim 1, wherein the first and second thermoelectric sensing elements have substantially equal Seebeck coefficients.

5. The flow sensing apparatus of claim 1, wherein the first and second thermoelectric sensing elements have equal Seebeck coefficients.

6. The flow sensing apparatus of claim 1, wherein the first thermoelectric sensing element has a Seebeck coefficient greater than a magnitude selected from the group consisting of about 200 μV/K, about 250 μV/K, about 300 μV/K, about 350 μV/K, about 400 μV/K, about 450 μV/K, about 500 μV/K, about 550 μV/K, about 600 μV/K, about 650 μV/K, about 700 μV/K, about 750 μV/K, about 800 μV/K, about 850 μV/K, about 900 μV/K, about 950 μV/K, about 1000 μV/K, about 1050 μV/K, about 1100 μV/K, about 1150 μV/K, about 1200 μV/K, about 1250 μV/K, about 1300 μV/K, about 1350 μV/K, about 1400 μV/K, about 1450 μV/K, about 1500 μV/K, about 1550 μV/K, about 1600 μV/K, about 1650 μV/K, about 1700 μV/K, about 1750 μV/K, about 1800 μV/K, about 1850 μV/K, about 1900 μV/K, about 1950 μV/K, and about 2000 μV/K.

7. The flow sensing apparatus of claim 1, wherein the second thermoelectric sensing element has a Seebeck coefficient greater than a magnitude selected from the group consisting of about 200 μV/K, about 250 μV/K, about 300 μV/K, about 350 μV/K, about 400 μV/K, about 450 μV/K, about 500 μV/K, about 550 μV/K, about 600 μV/K, about 650 μV/K, about 700 μV/K, about 750 μV/K, about 800 μV/K, about 850 μV/K, about 900 μV/K, about 950 μV/K, about 1000 μV/K, about 1050 μV/K, about 1100 μV/K, about 1150 μV/K, about 1200 μV/K, about 1250 μV/K, about 1300 μV/K, about 1350 μV/K, about 1400 μV/K, about 1450 μV/K, about 1500 μV/K, about 1550 μV/K, about 1600 μV/K, about 1650 μV/K, about 1700 μV/K, about 1750 μV/K, about 1800 μV/K, about 1850 μV/K, about 1900 μV/K, about 1950 μV/K, and about 2000 μV/K.

8. The flow sensing apparatus of claim 1, wherein the first and second thermoelectric sensing elements comprise one or more materials selected from the group consisting of: bismuth telluride, lead-germanium-selenium glasses, uranium oxides, thallium tin telluride, and thallium germanium telluride.

9. The flow sensing apparatus of claim 1, wherein the first and second thermoelectric sensing elements are discrete thermoelectric elements in an array of thermoelectric elements.

10. The flow sensing apparatus of claim 1, further comprising a controller that controls the power supplied to the heating element such that the heating element is maintained at a substantially constant temperature, wherein the controller is coupled to at least one of the first and the second thermoelectric sensing elements to sense the temperature of the heating element.

11. A method of sensing a flow rate through a fluid channel having a first thermoelectric sensing element and a second thermoelectric sensing element equally spaced along the fluid channel from heating element, the method comprising:

oppositely-doping material of the first and second thermoelectric sensing elements;

electrically connecting the first and second thermoelectric sensing elements in series so that temperature information from the first and second thermoelectric sensing elements is a highly sensitive response;

actuating the heating element;

flowing a sample through the fluid channel;

receiving the temperature information from the first thermoelectric sensing element and the second thermoelectric sensing element; and calculating a flow rate based on a difference in temperatures between the first thermoelectric sensing element and the second thermoelectric sensing element.

12. The method of claim 11, wherein the heating element is supplied with a constant-power power supply and
further comprising: controlling the power supplied to the heating element such that the temperature of the heating element is substantially constant.

13. The method of claim 11, wherein
the first thermoelectric sensing element has a Seebeck coefficient greater than a magnitude selected from the group consisting of about 200 μV/K, about 250 μV/K, about 300 μV/K, about 350 μV/K, about 400 μV/K, about 450 μV/K, about 500 μV/K, about 550 μV/K, about 600 μV/K, about 650 μV/K, about 700 μV/K, about 750 μV/K, about 800 μV/K, about 850 μV/K, about 900 μV/K, about 950 μV/K, about 1000 μV/K, about 1050 μV/K, about 1100 μV/K, about 1150 μV/K, about 1200 μV/K, about 1250 μV/K, about 1300 μV/K, about 1350 μV/K, about 1400 μV/K, about 1450 μV/K, about 1500 μV/K, about 1550 μV/K, about 1600 μV/K, about 1650 μV/K, about 1700 μV/K, about 1750 μV/K, about 1800 μV/K, about 1850 μV/K, about 1900 μV/K, about 1950 μV/K, and about 2000 μV/K and
the second thermoelectric sensing element has a Seebeck coefficient greater than a magnitude selected from the group consisting of about 200 μV/K, about 250 μV/K, about 300 μV/K, about 350 μV/K, about 400 μV/K, about 450 μV/K, about 500 μV/K, about 550 μV/K, about 600 μV/K, about 650 μV/K, about 700 μV/K, about 750 μV/K, about 800 μV/K, about 850 μV/K, about 900 μV/K, about 950 μV/K, about 1000 μV/K, about 1050 μV/K, about 1100 μV/K, about 1150 μV/K, about 1200 μV/K, about 1250 μV/K, about 1300 μV/K, about 1350 μV/K, about 1400 μV/K, about 1450 μV/K, about 1500 μV/K, about 1550 μV/K, about 1600 μV/K, about 1650 μV/K, about 1700 μV/K, about 1750 μV/K, about 1800 μV/K, about 1850 μV/K, about 1900 μV/K, about 1950 μV/K, and about 2000 μV/K.

14. A kit comprising:
(a) a flow sensing apparatus comprising:
a fluid channel that allows a fluid to flow in a first direction;
a first thermoelectric sensing element arranged at a first position along the fluid channel such that the first thermoelectric sensing element senses a temperature of the fluid, wherein the first thermoelectric sensing element is doped with a N-type charge carrier;
a second thermoelectric sensing element arranged at a second position along the fluid channel and separated from the first sensing element by a predetermined distance along the fluid channel, wherein the second thermoelectric sensing element is doped with a P-type charge carrier; and
a heating element arranged between the first and second thermoelectric sensing elements, the heating element being equally spaced from the first and second thermoelectric sensing elements; and (b) instructions for installation and/or use.

15. A High Performance Liquid Chromatography (HPLC) device comprising a flow sensing apparatus comprising:
   a fluid channel that allows a fluid to flow in a first direction;
   a first thermoelectric sensing element arranged at a first position along the fluid channel such that the first thermoelectric sensing element senses a temperature of the fluid;
   a second thermoelectric sensing element arranged at a second position along the fluid channel and separated from the first sensing element by a predetermined distance along the fluid channel;
   a heating element arranged at a heater position between the first and second thermoelectric sensing elements, the heating element being equally spaced from the first and second thermoelectric sensing elements; and
   an amplifier element coupled to the first and second thermoelectric sensing elements for sampling, subtracting and amplifying temperature measurements from the first and second thermoelectric sensing elements,
   wherein:
   at zero-flow condition, a temperature profile curve of temperature versus distance is symmetrical about the heater position; and
   the first position and the second position are at inflection points of the temperature profile curve so that an amount of time required to detect a difference between measured temperatures is minimized and, in turn, a response of the amplifier element to flow rate change is maximized.

16. The method of claim 11, further comprising the steps of:
   placing the first and second thermoelectric sensing elements adjacent and flush against each other on a first side of the fluid channel; and
   placing the heating element on a second side of the fluid channel opposing the first side.

\* \* \* \* \*